United States Patent [19]

Hirai et al.

[11] 4,252,958

[45] Feb. 24, 1981

[54] PROCESS FOR PREPARING 2,2,6,6-TETRAMETHYL-4-OXOPIPERIDINE

[75] Inventors: Bunji Hirai, Kuki; Naohiro Kubota, Urawa; Yutaka Nakahara, Iwatsuki, all of Japan

[73] Assignee: Argus Chemical Corporation, Brooklyn, N.Y.

[21] Appl. No.: 971,858

[22] Filed: Dec. 21, 1978

[30] Foreign Application Priority Data

Dec. 21, 1977 [JP]  Japan ................................. 52/154217
Feb. 23, 1978 [JP]  Japan ................................. 53/20337

[51] Int. Cl.³ ........................................... C07D 211/74
[52] U.S. Cl. ................................................... 546/242
[58] Field of Search ........................... 546/242; 252/438

[56] References Cited

U.S. PATENT DOCUMENTS

| | | | |
|---|---|---|---|
| 3,513,170 | 5/1970 | Murayama et al. | 546/242 |
| 3,953,459 | 4/1976 | Orban et al. | 546/242 |
| 3,963,730 | 6/1976 | Murayama et al. | 546/242 |

OTHER PUBLICATIONS

*Chemical Abstracts,* 44:5138f (1950) [Iguchi, T., *J. Soc. Rubber Ind. Japan,* 16, 771–774 (1943)].
*Chemical Abstracts,* 64:6506d (1966), [Borchert, French Patent 1,414,407, 10/15/65].
*Chemical Abstracts,* 84:180830m (1976), [Kamenskii, I., et al., *Zm. Prikl. Khim.,* 1976, 49(3), 628–630].

*Primary Examiner*—John D. Randolph
*Assistant Examiner*—Richard A. Schwartz
*Attorney, Agent, or Firm*—Otto S. Kauder

[57] ABSTRACT

There is disclosed a process for preparing 2,2,6,6-Tetramethyl-4-oxopiperidine (triacetoneamine), in which a hydrazine hydrohalide salt catalyzes the reaction of an acetone compound, for example acetone or diacetone alcohol, with an ammonia donor compound, for example ammonia or 2,2,4,4,6-pentamethyl-1,2,5,6-tetrahydropyrimidine (acetonine).

13 Claims, No Drawings

PROCESS FOR PREPARING 2,2,6,6-TETRAMETHYL-4-OXOPIPERIDINE

BACKGROUND OF THE INVENTION

This invention relates to a new process for the preparation of 2,2,6,6-tetramethyl-4-oxopiperidine, a known compound, sometimes referred to by the name triacetonamine. Triacetonamine has been recognized as a key intermediate in the preparation of certain 4-substituted 2,2,6,6-tetramethylpiperidine derivatives which are excellent in protecting synthetic resin compositions against the deleterious influences of heat and light. For an outline of how triacetonamine is used as intermediate in the preparation of effective stabilizers the disclosure of M. Minagawa et al in U.S. Pat. No. 4,124,564 of Nov. 7, 1978 can be consulted, particularly Col. 7 line 14 to Col. 9 line 30.

Triacetonamine has been known at least since the work of W. Heinz published in Annalen der Chemie, 1880, vol. 203, page 336. Heinz converted acetone to phorone (2,6-dimethylhepta-2,5-dien-4-one) in about 30% yield and this with ammonia to triacetonamine in 70% yield. H. K. Hall in Journal of the American Chemical Society, 1957, vol. 79, page 5447, described a reaction of acetone with ammonia in the presence of calcium chloride for 7 days that gave about 20% yield of triacetonamine after careful fractional distillation to separate the desired product from a different basic nitrogen compound having a nearby boiling point. R. B. Bradbury et al in Journal of the Chemical Society 1947, pages 1394-99, described reactions of acetone and ammonia, alone and with a number of different catalysts, that did not give any triacetonamine. Bradbury's product, obtained in 17% yield without catalyst and in 35% to 90% yield depending on catalyst choice was 2,2,4,4,6-pentamethyl-2,3,4,5-tetrahydropyrimidine hydrate, split to diacetonamine

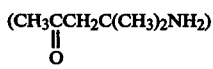

oxalate by the action of alcoholic oxalic acid.

K. Murayama in U.S. Pat. No. 3,513,170 of May 19, 1970 disclosed the conversion of Bradbury's pyrimidine (acetonine) to triacetonamine by the action of a Lewis acid in presence of water. Murayama's Lewis acids include zinc chloride, calcium chloride, and picric acid. In the same patent, Murayama also disclosed the use of diacetone alcohol or acetone with acetonine and/or ammonia, to prepare triacetonamine, as well as the reaction of triacetonamine with diacetone alcohol and calcium chloride under similar conditions to give a higher condensation product 1,9-diaza-2,2,8,8,10,10-hexamethyl-4-oxospiro(5,5) undecane having an empirical formula $C_{15}H_{28}N_2O$.

I. Orban in U.S. Pat. No. 3,943,139 of Mar. 9, 1976 disclosed preparation of triacetonamine by heating phorone with aqueous ammonia and basic catalysts, such as lithium, sodium, calcium, or barium hydroxide, in an autoclave under pressure.

I. Orban in U.S. Pat. No. 3,953,459 of Apr. 27, 1976 disclosed preparation of triacetonamine from acetonine with acetone or diacetone alcohol either in the presence or in the absence of water and an acidic catalyst such as boron trifluoride in a controlled amount of 0.2 to 12 mole % relative to the acetonin.

I. Orban in U.S. Pat. No. 3,959,295 of May 25, 1978 disclosed preparation of triacetonamine from ammonia and acetone or an acidic self-condensation product of acetone in the presence of acidic catalysts in two stages carried out at two different temperatures, such as about 15° C. in the first stage and 50°-55° C. in the second stage, with the amount of acetone being at least 1.6 moles per mole of ammonia.

K. Murayama in U.S. Pat. No. 3,959,298 of May 25, 1976 disclosed preparation of triacetonamine from acetonine and water in the presence of at least 0.125 mole acid catalyst per mole of acetonin. Catalysts included an acetonin salt, an ammonium salt, an amine salt, a mineral acid, or an organic acid.

I. Orban in U.S. Pat. No. 3,960,875 of June 1, 1976 disclosed the preparation of triacetonamine by heating acetonine with acetone or diacetone alcohol in an alcohol solvent without catalyst.

K. Murayama in U.S. Pat. No. 3,963,730 of June 15, 1976 disclosed preparation of triacetonamine by heating acetonine with acetone under anhydrous conditions using an ammonium or amine salt catalyst such as ammonium chloride, ammonium formate, acetonine hydrochloride, pyridine hydrochloride, a hydrochloric acid treated carboxylic acid type ion exchange resin, acetonineacetate, and urea nitrate.

Consideration of the above art as a whole leaves a confused and contradictory impression, with no clear indication of the nature of the key process variables or directions toward a practically workable process.

SUMMARY OF THE INVENTION

In accordance with this invention, 2,2,6,6-tetramethyl-4-oxopiperidine (referred to in the remainder of this disclosure as triacetonamine) is prepared by a catalytic process from an acetone compound and an ammonia donor compound, which comprises bringing together in the liquid phase at least one acetone compound and at least one dissimilar ammonia donor compound in the presence of a catalytically effective amount of a hydrazine hydrohalide having the formula $R_1R_2N-NR_3R_4 \cdot nHX$, in which independently each of $R_1$, $R_2$, $R_3$, and $R_4$ is an alkyl group having 1 to 18 carbon atoms, a cycloalkyl group having 4 to 20 carbon atoms, an aryl group having 6 to 18 carbon atoms, an alkaryl group having 7 to 21 carbon atoms, an aralkyl group having 7 to 21 carbon atoms, or hydrogen; X is bromine, chlorine, or iodine; and n is 1 or 2, and recovering triacetonamine from the reaction mixture.

The amount of catalytically effective hydrazine hydrohalide required is moderate. As little as 0.01% by weight of the acetone compound is effective, and a preferred range of use concentrations is from 0.05% to 10% by weight of the acetone compound. Larger amounts can be used but tend to be wasteful and uneconomic.

A number of materials function as co-catalysts when combined with the hydrazine hydrohalide catalyst of this invention, interacting beneficially to enable results better than with either ingredient of the combination alone to be obtained.

DESCRIPTION OF PREFERRED EMBODIMENTS

The acetone compound starting material for the preparation of triacetoneamine by the process of this invention can be acetone, a condensation product of acetone with itself such as diacetone alcohol, mesityl oxide, or phorone, and a condensation product of acetone with ammonia such as diacetonamine, triacetonediamine, or 2,2,4,4,6-pentamethyl-1,2,5,6-tetrahydropyrimidine (referred to in the remainder of this disclosure as acetonine). The ammonia donor compound starting material can be ammonia, and a condensation product of acetone with ammonia such as diacetonamine, triacetonediamine, or acetonin, provided that the acetone compound and the ammonia donor compound are not identical. A plurality of acetone compounds can be used in combination in the process of its invention, as can a plurality of ammonia donor compounds. Some combinations of starting materials that can be used according to this invention to prepare triacetonamine in the presence of a hydrazine hydrohalide catalyst include acetone with ammonia, diacetone alcohol with ammonia, acetonine with ammonia, acetone with diacetonamine, acetone with acetonine, mesityl oxide with acetonine, diacetone alcohol with triacetonediamine, acetone with ammonia and acetonine, mesityl oxide and phorone with ammonia, and diacetone alcohol and mesityl oxide with ammonia and diacetonamine.

In the formula of the hydrazine hydrohalide catalyst, alkyl groups $R_1$, $R_2$, $R_3$, and $R_4$ can be for example methyl, ethyl, propyl, isopropyl, n-butyl, isobutyl, sec-butyl, t-butyl, amyl, isoamyl, 2-ethylbutyl, h-hexyl, 4-methyl-2-pentyl, heptyl, octyl, isooctyl, 2-ethylhexyl, 3,5,5-trimethylhexyl, nonyl, decyl, isodecyl, undecyl, lauryl, myristyl, cetyl, and stearyl. Aryl groups $R_1$, $R_2$, $R_3$, and $R_4$ can be for example phenyl, naphthyl, anthracenyl, phenanthryl, biphenylyl, and terphenylyl. Cycloalkyl groups $R_1$, $R_2$, $R_3$, and $R_4$ can be for example cyclobutyl, cyclopentyl, dimethylcyclobutyl, methylcyclopentyl, cyclohexyl, 3-methylcyclohexyl, 3,3,5-trimethylcyclohexyl, 4-t-butylcyclohexyl, norbornyl, dihydrocyclopentadienyl, and dihydroabietyl and dehydroabietyl. Alkaryl groups $R_1$, $R_2$, $R_3$, and $R_4$ can be for example o-tolyl, m-tolyl, p-tolyl, 2,3-xylyl, 2,5-xylyl, 3,5-xylyl, 4-t-butylphenyl, 2-t-butyl-5-methylphenyl, octylphenyl, nonylphenyl, dodecyl-o-tolyl, pentadecylphenyl, dimethylnaphthyl, and diamylnaphthyl. Aralkyl groups $R_1$, $R_2$, $R_3$, and $R_4$ can be for example benzyl, 1-phenylethyl, 7-phenylheptyl, and p-dodecylbenzyl. Inert substituents can be carried on the $R_1$, $R_2$, $R_3$ and $R_4$ groups such as alkoxyl, nitro, and halogen as in 4-nitrophenyl, 3,4-dichlorophenyl, and 6,7-dimethoxynaphthyl.

Examples of the hydrazine hydrohalide catalysts indicated by the above general formula are mono or di salts of hydrogen bromide, chloride and iodide of hydrazine, N-methylhydrazine, N,N-dimethylhydrazine, N,N'-dimethylhydrazine, N-propylhydrazine, N-isopropylhydrazine, N,N-dipropylhydrazine, N,N'-dipropylhydrazine, N-butylhydrazine, N,N-dibutylhydrazine, N-methyl-N-butylhydrazine, N-cyclohexylhydrazine, N-phenylhydrazine, N-N-diphenylhydrazine, N-N'-di-phenylhydrazine, N,N,N'-triphenylhydrazine, N-benzylhydrazine, N-phenyl-N-benzylhydrazine, N-methyl-N-p-nitrophenylhydrazine, N-naphthylhydrazine.

Co-catalysts that can be used with hydrazine hydrohalide catalyst according to the invention include bromine and iodine; lithium, sodium and potassium bromide; lithium, sodium and potassium iodide; ammonium bromide and iodide; lithium and ammonium thiocyanate; ammonium sulfate, lithium nitrite, ammonium chloride, lithium cyanate; hydrobromide, hydroiodide, nitrite, methane sulfonate, benzenesulfonate and p-toluenesulfonate of urea and thiourea; maleic acid hydrazide, 2,2'-thiodiethanol, triethanolamine, dicyandiamide, barium hydroxide, and synthetic absorbent like magnesium silicate hydrate, aluminum silicate hydrate, activated carbon, and diatomaceous earth.

Moreover, Lewis acid catalysts known as catalyst for the preparation of triacetonamine can be combined with hydrazine hydrohalide catalysts of this invention for greater effectiveness than obtainable with either catalyst type alone.

When a co-catalyst is used together with the hydrazine hydrohalide catalyst in the process of this invention, the amount of co-catalyst is usually from 0.01 to 10% by weight of the acetone compound, preferably 0.1 to 5%.

The relative proportions of acetone compound and ammonia donor compound used in the preparation of triacetonamine by the process of this invention can be varied over a wide range. If desired, ammonia can be used in excess, as by saturating the reaction mixture with ammonia gas at normal or superatmospheric pressure or by charging liquid ammonia. With liquid ammonia donor compounds such as acetonin or diacetonamine, the molar ratio of acetone to ammonia donor compound can be from 0.1 to 1 to greater than 1:1, preferably 1:1 to 10:1, with excess acetone functioning as reaction solvent.

The reactants, catalyst, co-catalyst when used, solvent and so on can be charged all at once or in several portions as the reaction proceeds.

The process of the invention is carried out in the liquid phase at any temperature and pressure at which the reaction mixture is liquid. Preferably, the reaction temperature is between 0° C. and the boiling point of the reaction mixture, with a range of 30°–60° C. particularly preferred. Such a temperature is easily established by beginning the reaction at room temperature when acetone is used as the acetone compound starting material, and heating the reaction mixture to the reflux temperature of boiling acetone. For particularly rapid operation, the reaction temperature can be adjusted to 70°–110° C. by the use of higher boiling starting materials (e.g. diacetone alcohol, phorone, acetonin) as well as by working at superatmospheric pressure up to 30 atmospheres, preferably 1 to 5 atmospheres.

The required reaction time ranges from about 3 to about 20 hours, in inverse relationship to the reaction temperature.

The use of solvent in the preparation of triacetonamine by the process of this invention is not critical but can be carried out if desired. Solvents that can be used, for example, are aliphatic hydrocarbons such as pentane, hexane; cyclohydrocarbons such as cyclohexane; aromatic hydrocarbons such as benzene, toluene, xylene; chlorinated hydrocarbons such as methylene chloride, 1,1,1-trichloroethane, carbon tetrachloride; nitriles such as acetonitrile; neutral polar solvents such as sulpholane, nitromethane, dimethylformamide, dimethylacetamide, tetramethylurea, hexamethylphosphoric acid triamide, dimethylsulfoxide; alcohols such as methanol, ethanol, isopropanol, butanol, tert-butanol, 2-ethylhexanol, cyclohexanol, benzyl alcohol, ethylene glycol, diethylene glycol, propylene glycol, ethylene glycol monomethyl ether, ethylene glycol monoethyl ether; ketones such as acetone, methylethylketone, diethylketone, methyl-n-propylketone, di-n-propylketone, diisopropylketone, di-n-butylketone, acetylacetone, hexane-2,5-dione, cyclohexanone, diacetone alcohol, mesityl oxide; ethers such as tetrahydrofurane, dioxane, diethyl ether.

In the preparation of triacetonamine according to the process of this invention, the presence or absence of water is not critical. It is not necessary to add any water nor to take pains to exclude it. Some water is formed as a product of the reaction between acetone and ammonia; such water can be removed as it forms, or allowed to accumulate and become part of the solvent system. At the end of the reaction, the lowest boiling components of the mixture are unreacted acetone, water, and solvent, if used; these can be stripped and used in subsequent preparations without separation from one another.

Triacetonamine can be recovered from the reaction mixture by conventional techniques, for example by precipitation as the hydrate by adding water, or by precipitation of a hydrohalide, sulfate, or oxalate salt by adding the appropriate acid, or by distillation suitably after adding an excess of strong alkali such as concentrated potassium or sodium hydroxide solution.

The following examples are by way of illustration and not by way of limitation.

EXAMPLE 1

A flask having attached a Dimroth condenser and a gas inlet tube was charged with acetone 180 g, methanol 9 g, N,N'-dimethylhydrazine dihydrochloride 1.8 g and ammonia gas was introduced for 5 hours at 40°–45° C. while stirring. Then, the ammonia gas was stopped and the mixture kept 15 hours at the same temperature, while the colorless clear liquid turned to light red by way of yellow. The reaction mixture was stripped in vacuo and left a light red residue. Triacetonamine 93.0 g was obtained by vacuum distillation (yield 58% based on acetone supplied).

This Example demonstrates the preparation and recovery in high yield of triacetonamine by a process according to this invention.

EXAMPLE 2

Into a mixture of 50 g acetone and 1.8 g hydrazine monohydrochloride was introduced ammonia gas for 4 hours at 40°–45° C., then was added 130 g acetone and allowed to react for 15 hours at 40°–45° C. The product was treated in the same procedure as in Example-1 to obtain 105.8 g of triacetonamine (yield: 66%).

This Example demonstrates the preparation and recovery in high yield of triacetonamine by a process according to this invention.

EXAMPLE 3

Into a mixture of 350 g acetone, 8.5 g water and 17.5 g N-phenylhydrazine monohydrochloride was introduced ammonia gas for 5 hours at 30°–35° C. After stopping the gas supply, the mixture was warmed to 50°–55° C. and left to react for 12 hours. After solvent removal in vacuo, light-red residue was mixed with acetone and introduced hydrogen chloride gas until pH=7. The crystals precipitated were filtered out, washed with water, and there was obtained 211.9 g of triacetonamine hydrochloride.

This Example demonstrates the preparation and recovery in high yield of triacetonamine in the form of the hydrochloride salt by a process according to this invention.

EXAMPLES 4 to 9

Into a mixture of 270 g acetone, 13.5 g methanol and 2.7 g of each catalyst mentioned below was introduced ammonia gas for 4 hours at 45°–50° C. After the end of the gas introduction, the mixture was kept 15 hours at the same temperature to complete the reaction. Then, the reaction solution was analyzed by gas chromatography, and the following results were obtained. For controls, zinc chloride and ammonium chloride as examples of Lewis acids were used.

| NO. | | CATALYST | YIELD OF TRIACETONAMINE g |
|---|---|---|---|
| Control | 1 | Zinc chloride | 52.9 |
| | 2 | Ammonium chloride | 81.8 |
| | 3 | None | None |
| EXAMPLE | 4 | N-methylhydrazine monohydrochloride | 144.3 |
| | 5 | N-naphthylhydrazine dihydrochloride | 134.7 |
| | 6 | N,N,N'-triphenylhydrazine hydrochloride | 129.9 |
| | 7 | Hydrazine hydrobromide | 125.1 |
| | 8 | N,N-dibutylhydrazine hydrobromide | 120.3 |
| | 9 | N-isopropylhydrazine hydrobromide | 120.4 |

The results of these Examples demonstrate the importance of using a catalyst and the superior catalytic effectiveness of hydrazine hydrohalide catalysts in the preparation of triacetonamine by the process of this invention compared to prior art catalysts.

EXAMPLE 10

Into a mixture of 180 g of acetone, 9 g of dimethylformamide and 5.5 g of hydrazine dihydrochloride was introduced ammonia gas for 1 hour while maintaining at 40°–45° C.

After stopping the gas, the mixture was reacted for 2 hours at the same temperature, then again introduced ammonia gas for 1 hour. This process was repeated four times. After the last introduction, the reaction was continued for 10 hours at the same temperature to obtain 115.8 g of triacetonamine recovered as in Example 1.

This Example demonstrates the preparation and recovery in high yield of triacetonamine by a process according to this invention in which the catalyst is a hydrazine dihydrohalide and a solvent is used.

EXAMPLE 11 to 16

Into mixtures of 255 g acetone, 13 g benzene, 0.8 g hydrazine dihydrochloride and 1.3 g of each co-catalyst mentioned below was introduced ammonia gas for 6 hours while maintaining 15°–20° C.

The gas, was stopped and the temperature raised to 50°–55° C. and kept there for 18 hours.

The reaction solution obtained was analyzed by gas chromatography in the same way as Example 4.

| No. | Co-Catalyst | Yield of Triacetonamine g. |
|---|---|---|
| Example 11 | None | 138.6 |
| Example 12 | Potassium iodide | 159.0 |
| 13 | Ammonium sulfide | 152.2 |

-continued

| No. | Co-Catalyst | Yield of Triacetonamine g. |
|---|---|---|
| 14 | Thiodiethanol | 150.0 |
| 15 | Lithium bromide | 154.5 |
| 16 | Maleic acid hydrazide | 161.3 |

The results of these examples, taken together with the results of Examples 4 to 9 and Controls 1 and 2 above, show the unexpected enhanced effectiveness of hydrazine hydrohalide-cocatalyst combinations in increasing the yield of triacetonamine obtainable by a process according to this invention.

EXAMPLE 17

An autoclave was charged with 180 g of acetone and 1.8 g of N-butylhydrazine monohydrochloride. The head space gas was replaced completely with ammonia gas and the mixture reacted for 2 hours at 90° C. while stirring.

The autoclave was returned to the normal pressure, and the reaction continued for 12 hours under the reflux of the unreacted acetone.

In the reaction solution 101.0 g of triacetonamine was produced according to gaschromatography.

This Example demonstrates the preparation in high yield of triacetonamine by a process of this invention operated at superatmospheric pressure at a temperature higher than the normal boiling point of acetone.

EXAMPLES 18 TO 20

The process as in Example 1 was carried out and the yield of triacetonamine determined by gas chromatography except that the amount shown of N-benzylhydrazine hydrobromide was used as catalyst.

| No. | AMOUNT OF CATALYST | YIELD OF TRIACETONAMINE |
|---|---|---|
| EXAMPLE 18 | 0.45g | 83.4g |
| 19 | 1.8 | 89.8 |
| 20 | 3.6 | 91.4 |

These Examples demonstrate the preparation in high yield of triacetonamine by a process according to this invention in which the use concentration of the hydrazine hydrohalide catalyst is varied over an eightfold range.

EXAMPLES 21 to 24

To examine the combined effects of the hydrazine hydrohalide catalyst of the invention with a known catalyst for production of triaceton amine, N-methyl-N-nitrophenyl hydrazine hydrochloride 1.8 g, acetone 50 g, dioxane 9 g and prior catalyst 1.8 g were treated with NH₃ gas for 4 hours while cooling at 10°-15° C. The gas was stopped, there was added 130 g of acetone, and the reaction continued at 50°-55° C. for 20 hours, and the solution analyzed to determine the yield of triacetonamine.

| No. | SECOND CATALYST | YIELD OF TRIACETONAMINE g |
|---|---|---|
| EXAMPLE 21 | None | 85.0 |
| 22 | Ammonium chloride | 99.4 |
| 23 | Zinc chloride | 93.0 |
| 24 | Boron trifluoride ether solution | 96.2 |

The results of these examples, taken together with the results of Examples 4 to 9 and Controls 1 and 2 above, show the unexpected beneficial effect of using known catalysts as second catalyst together with hydrazine hydrohalide according to this invention in increasing the yield of triacetonamine.

EXAMPLE 25

83 g of acetone, 15 g of isopropanol and 3 g of N-cyclohexylhydrazine hydroiodide were maintained at 45°-50° C. while adding dropwise 217 g of acetone and introducing ammonia gas during 3 hours. After stopping the gas, the reaction was continued for 12 hours at the same temperature to obtain 144.3 g of triacetonamine.

The results of this Example demonstrate the effectiveness of a cycloaliphatic hydrazine hydrohalide catalyst in the preparation of triacetonamine by a process according to this invention in high yield.

EXAMPLE 26

Into a mixture of 50 g of acetone, 130 g of diacetone alcohol and 3 g of N-phenyl-N-benzyl hydrazine hydrochloride were introduced ammonia gas for 8 hours at the room temperature. For the initial period, the temperature rose to about 50° C. by exothermic heat.

After stopping the gas, the mixture was reacted for 18 hours under the reflux of acetone, to obtain 88.2 g of triacetonamine.

The results of this Example demonstrate the effectiveness of an aromatic hydrazine hydrohalide catalyst in the preparation of triacetonamine in high yield by a process according to this invention in which diacetone alcohol is used as an acetone compound starting material.

EXAMPLE 27

Into a mixture of 680 g acetone, 130 g ethanol and 24 g hydrazine dihydrochloride was introduced ammonia gas for 5 hours while maintaining at 40°-45° C.

After stopping the gas, 1800 g of acetone, and 12 g of hydrazine dihydrochloride was added and reacted for 15 hours at the same temperature.

In the reaction solution obtained there was produced 1546.4 g of triacetonamine by gas chromatography.

The results of this Example demonstrate the preparation in high yield of triacetonamine by a process according to this invention.

EXAMPLES 28–31

To the mixture of 165 g acetone, 6 g N-(3-methylphenyl)hydrazine monohydrochloride and co-catalyst as shown below was introduced ammonia gas for 5 hours, while maintaining the temperature at 20°-25° C.

After stopping the gas, there was 430 g of acetone and 8.9 g of N-(3-methylphenyl)hydrazine monohydrochloride and the mixture was reacted at 50°-55° C. for the first 5 hours and then continued for 12 hours under the reflux of acetone. The yield of triacetonamine was determined by gas chromatographic analysis.

| NO. | Co-Catalyst | | Yield of Triaceton-amine g |
|---|---|---|---|
| Example 28 | Barium hydroxide octahydrate | 8.9g | 333.9 |
| Example 29 | Triethanol amine | 29.8 | 344.5 |
| 30 | Diatomaceous earth | 21.4 | 318.0 |
| 31 | Iodine | 16.7 | 339.2 |

The results of these Examples demonstrate the preparation in high yield of triacetonamine by a process in which a hydrazine hydrohalide catalyst and a co-catalyst are used according to this invention.

EXAMPLE 32

A flask with attached condenser was charged with 80 g of acetonine, 80 g of acetone, 16 g methanol and 1.6 g N-phenylhydrazine monohydrochloride and the mixture reacted at 50°–55° C. for 18 hours, while stirring. The reaction solution was stripped under reduced pressure, to obtain a light red residue. This residue was distilled in vacuo to obtain 60.4 g of triacetonamine. White crystals were obtained by recrystallization from petroleum ether having the melting point of 34°–36° C. The compound was confirmed to be the objective matter by IR spectrum and gas chromatography.

EXAMPLE 33

The mixture of 104 g of acetonine, 156 g of acetone and 1.0 g of N-(4-methylphenyl)hydrazine hydrochloride was reacted under the reflux of acetone for 15 hours. Then, 70.1 g of objective matter was obtained in the same way as in Example 32.

The results of Examples 32 and 33 demonstrate the preparation in high yield of triacetonamine by a process in which a hydrazine hydrohalide is used as catalyst with acetone and acetonine as the ammonia donor compound according to this invention.

EXAMPLE 34

A mixture of 95 g of acetonine hydrate, 165 g of acetone, 0.17 g of N,N'-dibutylhydrazine hydrochloride and 2.5 g of maleic acid hydrazide was reacted at 50°–55° C. for 20 hours. Then, 61.6 g of triacetonamine was obtained in the same process as in Example 32.

The results of this Example demonstrate the preparation in high yield of triacetonamine by a process including the use of a hydrazine hydrohalide catalyst and maleic hydrazide co-catalyst with acetone and acetonine as the ammonia donor compound starting material.

EXAMPLE 35

A mixture of 83 g of acetonine, 167 g of acetone, 17 g of water and 4.2 g of N,N'-dimethylhydrazine dihydrochloride was reacted at 50°–55° C. for 15 hours and then stripped under reduced pressure, followed by addition of acetone to the light-red residue and hydrogen chloride gas to pH=7. The crystals precipitated were filtered, washed with acetone, and dried to give 72.2 g of triacetonamine hydrochloride.

The results of this Example demonstrate the preparation in high yield of triacetonamine, recovered in the form of the hydrochloride salt, by a process using a hydrazine hydrohalide catalyst, acetone, and acetonine as the ammonia donor compound starting material in accordance with this invention.

EXAMPLE 36

The same reaction as in Example 32 except that using 80 g of diacetone alcohol instead of acetone was carried out and obtained 58.8 g of objective matter.

The results of this example demonstrate the preparation in high yield of triacetonamine by a process according to this invention in which diacetone alcohol and acetonine are used as the acetone compound and ammonia donor compound starting materials respectively.

EXAMPLES 37–41

A mixture of acetonine 110 g, acetone 330 g, 10 g benzene and 3.3 g of each catalyst listed below was reacted under the reflux of acetone for 15 hours. As the reaction solution were analyzed by gas chromatography, triacetone amine had been produced in the amount shown.

| EX. NO. | | CATALYST | YIELD OF TRIACETON-AMINE |
|---|---|---|---|
| Control | 4 | None | 5.3 |
| | 5 | Ammonium Chloride | 51.6 |
| EXAMPLE | 37 | N-methyl-N-butylhydrazine hydrochloride | 78.6 |
| | 38 | N-butylhydrazine di-hydrochloride | 85.2 |
| | 39 | N,N'-dimethylhydrazine di-hydrochloride | 83.0 |
| | 40 | Hydrazine hydrobromide | 77.5 |
| | 41 | N-isopropylhydrazine hydrobromide | 73.1 |

The results of these examples demonstrate the preparation in high yield of triacetonamine by a process of this invention in which various hydrazine hydrohalide catalysts are used.

EXAMPLE 42

A mixture of 70 g acetonine, 40 g dioxane, 0.4 g N-(3-methylphenyl)hydrazine hydrochloride and 4 g activated carbon was stirred at 40°–45° C. and treated drop by drop with 140 g acetone for 3 hours.

After the dropping addition the reaction mixture was warmed to 50°–55° C. and reacted further for 12 hours. The solution obtained was analyzed by GC and confirmed to contain triacetonamine.

The results of this Example demonstrate the successful use of a hydrazine hydrohalide catalyst and activated carbon co-catalyst in the process of this invention.

EXAMPLES 43 to 49

So as to examine the effect of co-catalysts, a mixture of 100 g acetonine, 150 g acetone, 0.4 g N-naphthylhydrazine hydrochloride and 5 g of co-catalysts shown below was reacted at 50°–55° C. for 17 hours.

The following results were obtained according to the GC analysis.

| EX. NO. | Co-catalysts | YIELD OF TRIACETONAMINE |
|---|---|---|
| 43 | None | 68.4 |
| 44 | Barium oxide | 80.5 |
| 45 | Lithium nitrite | 77.5 |
| 46 | Thiodiethanol | 78.5 |

-continued

| EX. NO. | Co-catalysts | YIELD OF TRIACETONAMINE |
|---|---|---|
| 47 | Dicyandiamide | 80.4 |
| 48 | Triethanolamine | 83.6 |
| 49 | Ammonium iodide | 82.9 |

The results of these Examples confirm the successful use of a hydrazine hydrohalide catalyst together with each of several co-catalysts in the preparation of triacetonamine by a process according to this invention.

EXAMPLE 50

A mixture of 480 g acetonine, 520 g acetone, 240 g isopropanol and 5 g N,N,N'-triphenylhydrazine hydrochloride was reacted at 45°–50° C. for 3 hours.

Then there was added 300 g of acetone and reacted at the same temperature for 3 hours. This process was repeated twice and after the last addition of acetone the reaction was continued for 6 hours at the same temperature. The reaction solution obtained was analyzed and contained 352.7 g of triacetonamine.

The results of this Example demonstrate the successful use of a triarylhydrazine hydrohalide catalyst and an organic solvent in the preparation of triacetonamine by a process according to this invention.

EXAMPLES 51 to 54

So as to examine the combination effect of hydrazine hydrohalide catalyst with Lewis acid, a mixture of 90 g acetonine, 180 g acetone, 0.5 g N-benzylhydrazine hydrobromide and less than 0.5 g of Lewis acids below mentioned was reacted under the reflux of acetone for 13 hours.

The following results are obtained by the GC analysis of the reaction mixture for contained triacetonamine.

| EX. NO. | LEWIS ACIDS | YIELD OF TRIACETONAMINE |
|---|---|---|
| 51 | None | 58.9 |
| 52 | Zinc Chloride | 70.7 |
| 53 | Ammonium Chloride | 81.4 |
| 54 | Calcium Chloride | 73.4 |

The results of these Examples show the unexpected benefit of using a Lewis Acid as a second catalyst together with a hydrazine hydrohalide in the preparation of triacetonamine by a process according to this invention.

EXAMPLE 55

An autoclave was charged with acetonine 120 g, acetone 120 g, dimethylformamide 25 g and 1.2 g of hydrazine di-hydrochloride and reacted at 85° C. for 5 hours. After return to normal pressure, the reaction solution was analyzed by GC and found to contain 99.1 g of the intended product triacetonamine.

The results of this Example demonstrate the successful use of a hydrazine hydrohalide catalyst in the preparation of triacetonamine for acetone and acetonine as ammonia donor compound at a temperature above the normal boiling of acetone and pressure above atmospheric to maintain the liquid phase.

EXAMPLE 56

80 g of acetonine, 580 g of acetone, 24 g of water and 1.9 g of N-phenylhydrazine hydrochloride were reacted at 50°–55° C. for 3 hours. Then, 50 g of acetonine and 1.3 g of catalyst were added to the reaction solution and reacted for 3 hours. This procedure was repeated twice and the last addition of acetonine and catalyst the reaction was continued for 10 hours at the same temperature and obtained 185.2 g of triacetonamine after stripping and vacuum distillation.

The results of this example demonstrate the successful use of a semi-continuoustechnique in the preparation of triacetonamine from acetone, acetonine as the ammonia donor compound, and a hydrazine hydrohalide catalyst according to this invention.

We claim:

1. A process for preparing 2,2,6,6-tetramethyl-4-oxopiperidine by the catalyzed reaction of an acetone compound and an ammonia donor compound, comprising bringing together in the liquid phase at least one acetone compound selected from the group consisting of acetone, a condensation product of acetone with itself, and a condensation product of acetone with ammonia and at least one ammonia donor compound not identical with the acetone compound selected from the group consisting of ammonia and a condensation product of acetone with ammonia in the presence of a catalytically effective amount of hydrazine hydrohalide having the formula $R_1R_2N-NR_3R_4 \cdot nHX$ in which independently each of $R_1$, $R_2$, $R_3$, and $R_4$ is an alkyl group having 1 to 18 carbon atoms, a cycloalkyl group having 4 to 20 carbon atoms, an aryl group having 6 to 18 carbon atoms, an alkaryl group having 7 to 21 carbon atoms, an aralkyl group having 7 to 21 carbon atoms, or hydrogen; X is bromine, chlorine or iodine; and n is 1 or 2, and recovering 2,2,6,6-tetramethyl-4-oxopiperidine from the reaction mixture.

2. A process according to claim 1 in which the acetone compound is acetone.

3. A process according to claim 1 in which the acetone compound is diacetone alcohol.

4. A process according to claim 1 in which the ammonia donor compound is ammonia.

5. A process according to claim 1 in which the ammonia donor compound in acetonine.

6. A process according to claim 1 in which the quantity of hydrazine hydrohalide is from 0.05 to 10% by weight of the acetone compound.

7. A process according to claim 1 in which in the formula of the hydrazine hydrohalide $R_1$, $R_2$, $R_3$, and $R_4$ are hydrogen.

8. A process according to claim 1 in which the formula of the hydrazine hydrohalide at least one R is alkyl.

9. A process according to claim 1 in which in the formula of the hydrazine hydrohalide at least one R is aryl.

10. A process according to claim 1 in which in the formula of the hydrazine hydrohalide at least one R is cycloalkyl.

11. A process according to claim 1 in which in the formula of the hydrazine hydrohalide at least one R is aralkyl.

12. A process according to claim 1 in which 0.1 to 5% by weight of the acetone compound of a co-catalyst is present.

13. A process according to claim 12 in which the co-catalyst is selected from the group consisting of bromine and iodine; chloride, bromide, and iodide of lithium, sodium, potassium, and ammonium; lithium and ammonium sulfates and thiocyanates; hydrobromides, hydroidides, nitrites, methanesulfonates, benzensulfonates, and toluenesulfonates of urea and thiourea; maleic acid hydrazide; thiodiethanol and triethanolamine; barium oxide and hydroxide; synthetic absorbents; and Lewis acids.

* * * * *